United States Patent [19]

Miura et al.

[11] Patent Number: 4,959,356
[45] Date of Patent: Sep. 25, 1990

[54] PORPHYRINS FOR BORON NEUTRON CAPTURE THERAPY

[75] Inventors: Michiko Miura, Center Moriches, N.Y.; Detlef Gabel, Bremen, Fed. Rep. of Germany

[73] Assignee: The United States of America as represented by the United States Department of Energy, Washington, D.C.

[21] Appl. No.: 357,452

[22] Filed: May 26, 1989

[51] Int. Cl.$^5$ .......................... A61K 31/69; C07F 5/05
[52] U.S. Cl. ....................................... 514/64; 540/145
[58] Field of Search ........................... 540/145; 514/64

[56] References Cited

U.S. PATENT DOCUMENTS

| | | | |
|---|---|---|---|
| 2,858,320 | 10/1958 | Woods et al. | 260/314 |
| 4,386,087 | 5/1983 | Lavallee | 424/245 |
| 4,500,507 | 2/1985 | Wong | 424/1.1 |
| 4,516,535 | 5/1985 | Russell et al. | 128/1.1 |
| 4,675,338 | 6/1987 | Bommer et al. | 514/410 |
| 4,693,885 | 9/1987 | Bommer et al. | 424/2 |

OTHER PUBLICATIONS

BNL Report 41098, Miura et al., "Synthesis of New Boron Containing Porphyrins and Their In Vivo Properties", presented at the 3rd International Symposium on Neutron Capture Therapy, Bremen, West Germany, May 31–Jun. 3, 1988.
Fairchild et al., Chemical Abstracts, vol. 103 (1983) 67545w.
Ponomareo et al., Chemical Abstracts, vol. 98 (1982) 89034h.
Imamura et al., Chemical Abstracts, vol. 94 (1981) 113624r.
Ponomareo et al., Chemical Abstracts, vol. 84 (1976) 1055596.

*Primary Examiner*—Richard L. Raymond
*Attorney, Agent, or Firm*—Margaret C. Bogosian; James W. Weinberger; William R. Moser

[57] ABSTRACT

Novel compounds for treatment of brain tumors in Boron Neutron Capture Therapy are disclosed. A method for preparing the compounds as well as pharmaceutical compositions containing said compounds are also disclosed. The compounds are water soluble, non-toxic and non-labile boronated porphyrins which show significant uptake and retention in tumors.

12 Claims, No Drawings

PORPHYRINS FOR BORON NEUTRON CAPTURE THERAPY

This invention was made with Government support under contract number DE-AC02-76CH00016, between the U.S. Department of Energy and Associated Universities, Inc. The Government has certain rights in the invention.

BACKGROUND OF THE INVENTION

Cancer continues to be one of the foremost health problems. Conventional treatments such as surgery, radiation therapy and chemotherapy have been extremely successful in certain cases; in other instances, much less so. A much less familiar, alternative form of cancer therapy known as Boron Neutron Capture Therapy (BNCT) is being investigated to treat certain tumors for which the conventional methods are to date ineffective. BNCT has been used clinically in Japan to treat Glioblastoma multiforme, a highly malignant, invasive form of brain cancer.

In BNCT of malignant brain tumors, the patient is injected with a boron compound highly enriched in boron-10. The boronated compound concentrates preferentially in the brain tumor, while the action of the blood-brain barrier prevents its entry into the healthy surrounding tissues. The patient's head is then irradiated with a beam of thermal neutrons that are captured by the boron concentrated in the tumor. The tumor is thus irradiated with high LET alpha and Li particles whose range in tissue is about $10\mu$, or the diameter of an average cell. Therefore, a very localized, specific reaction takes place whereby the tumor receives a large radiation dose, compared to that received by the surrounding healthy tissue, from the transit of the thermal neutrons.

Several criteria must be met in order for BNCT to be successful. These include:

(1) the boron must be in high concentration at the tumor site (about 30 $\mu g^{10}B$/g tissue);

(2) there should be high selectivity of the drug for tumor over blood with tumor-to-blood ratios greater than two; and (3) the boronated drug itself should not be toxic. The second criteria above can usually be satisfied if the boronated drug does not penetrate the normal blood brain barrier.

In the clinical practice of BNCT in Japan to treat glioblastoma, $Na_2B_{12}H_{11}SH$ (BSH) is used as the boron-containing drug. However, in vitro experiments show that BSH does not stay in the tumor cell but is easily washed out, which may account for the lack of success in some of the trials with this material.

Porphyrins, in contrast, are retained in tumors for days to weeks and have an affinity for various types of cancers. It is therefore an object of this invention to provide new boronated drugs for BNCT that overcome the problems of the prior art materials and that take advantage of these characteristics of the porphyrin molecule.

U.S. Pat. No. 4,516,535 (Russell, Jr., et al) provides a broadly defined disclosure relating to the tumor affinity agent and the source of radioactivity used in BNCT, but only employs a boron hydride cage.

U.S. Pat. No. 4,500,507 (Wong) discloses technetium-labeled porphyrin and its use as a radio-active tracer in scintographic imaging techniques.

U.S. Pat. Nos. 4,675,338 (Bommer, et al) and 4,693,885 (Bommer, et al) are two of many patents which disclose novel porphyrin compounds for use as photosensitive agents in the treatment of tumors.

U.S. Pat. No. 2,858,320 (Woods, et al) discloses the use of hematoporphyrin in delineating cancerous tissue.

U.S. Pat. No. 4,386,087 (Lavallee) discloses N-methyl porphyrin and its use in the chemotherapeutic treatment of cancer.

The present invention is directed to new low toxicity boronated porphyrin compounds and a method for their use in BNCT. A process for preparing the boronated porphyrin compounds and compositions containing such compounds are also disclosed. These porphyrin compounds can be employed as vehicles for the transport of boron to malignant tumors especially brain tumors. The blood-brain barrier in mammals excludes the uptake of boronated porphyrin in normal brain cells and allows accumulation of said porphyrins in tumorous cells, so that upon irradiation significant damage will be done to the tumor cells while little damage will be done to the healthy surrounding tissue.

DETAILED DESCRIPTION OF THE INVENTION

Porphyrins are naturally occurring tetrapyrrole compounds normally found in plants and animals. They perform many vital biological functions by combining with metallic ions to produce a metalloporphyrin. Examples of bindable metal ions are iron, magnesium, manganese and zinc. Metalloporphyrins are essential for the normal metabolism of plants and animals. Hemin is the iron-containing porphyrin essential to mammalian blood, and chlorophyll is the magnesium-containing porphyrin that catalyzes photosynthesis. Other important metalloporphyrins are present in myogloblin, vitamin B-12, cytochrome, catalase and peroxidase.

The preferential affinity of porphyrins and metalloporphyrin for neoplastic tissue has been known for quite some time. When injected into tumor-bearing mammals, the porphyrins or metalloporphyrin accumulate in the tumors as shown by a brilliant fluorescence which is produced by ultra violet (UV) light activation of said porphyrins or metalloporphyrin.

In addition, natural porphyrins (un-symmetrical, beta substituted with no meso substituents resembling hemin in structure) have not shown toxicity in applications such as photodynamic therapy. The new boronated porphyrins of the present invention take advantage of these two important characteristics of prior art porphyrin compounds.

The present invention relates to a novel family of porphyrin compounds of the formula In the compounds of formula I, the preferred alkyl group is methyl and n is preferably 0.

These compounds are prepared following the synthetic route depicted in Reaction Scheme 1.

REACTION SCHEME 1

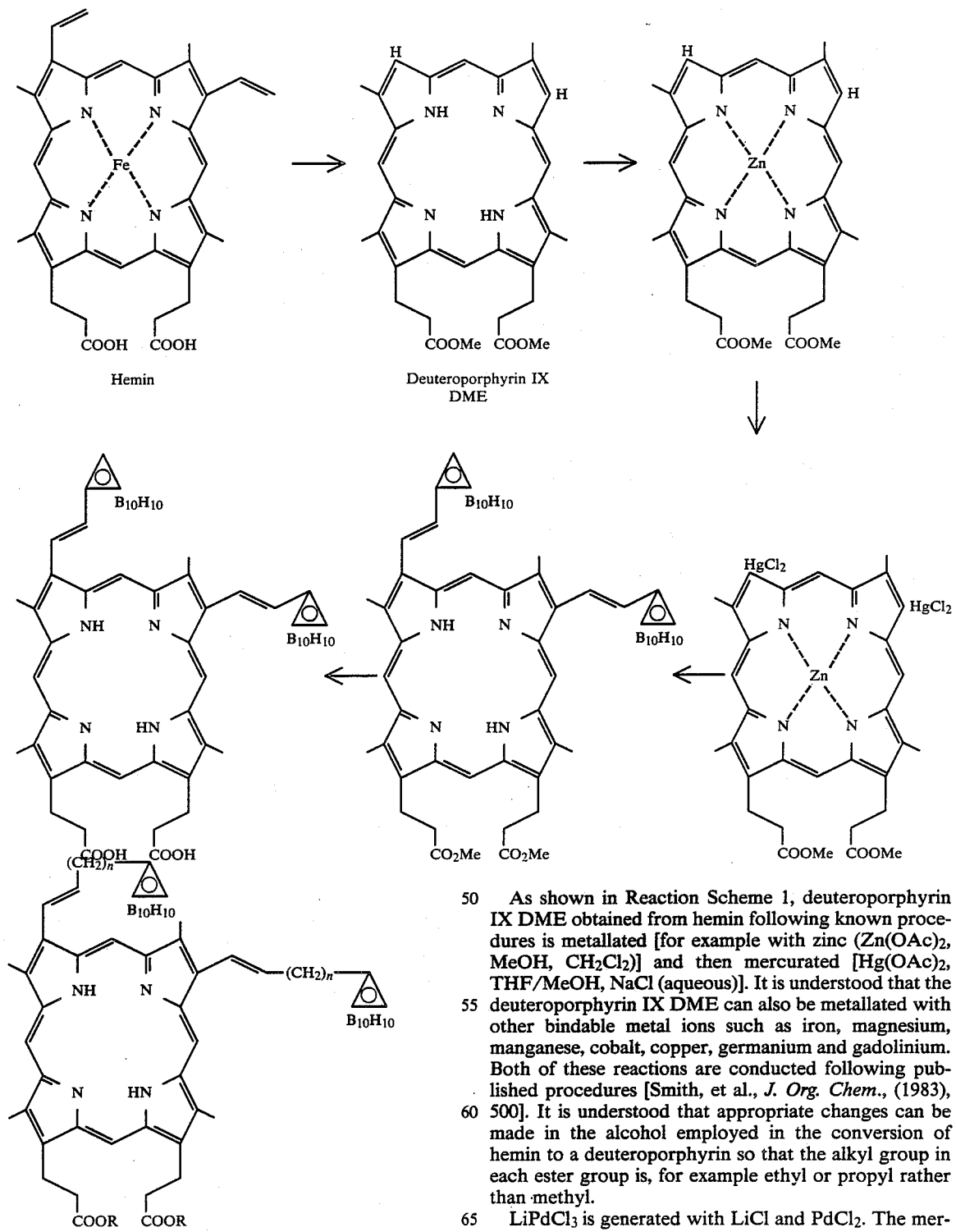

wherein R is hydrogen or lower alkyl containing 1 to 6 carbon atoms and n is 0 to 10.

As shown in Reaction Scheme 1, deuteroporphyrin IX DME obtained from hemin following known procedures is metallated [for example with zinc ($Zn(OAc)_2$, MeOH, $CH_2Cl_2$)] and then mercurated [$Hg(OAc)_2$, THF/MeOH, NaCl (aqueous)]. It is understood that the deuteroporphyrin IX DME can also be metallated with other bindable metal ions such as iron, magnesium, manganese, cobalt, copper, germanium and gadolinium. Both of these reactions are conducted following published procedures [Smith, et al., *J. Org. Chem.*, (1983), 500]. It is understood that appropriate changes can be made in the alcohol employed in the conversion of hemin to a deuteroporphyrin so that the alkyl group in each ester group is, for example ethyl or propyl rather than methyl.

$LiPdCl_3$ is generated with LiCl and $PdCl_2$. The mercurated porphyrin is stirred under $N_2$ as the $LiPdCl_3$ solution is added, followed by the addition of an alkenyl carborane wherein the alkenyl moiety contains at least two carbon atoms. In Reaction Scheme 1, vinyl carborane is used to introduce the boron cage.

The resulting carborated zinc complex (not shown in Reaction Scheme 1) is purified and the zinc is then removed using trifluoroacetic acid (TFA) under $N_2$ to produce the dimethyl ester. The dimethylester is then hydrolyzed to yield the diacid.

The solubility of the compounds of formula I in water can be increased by degrading the carborane cages, thus yielding compounds of the formula

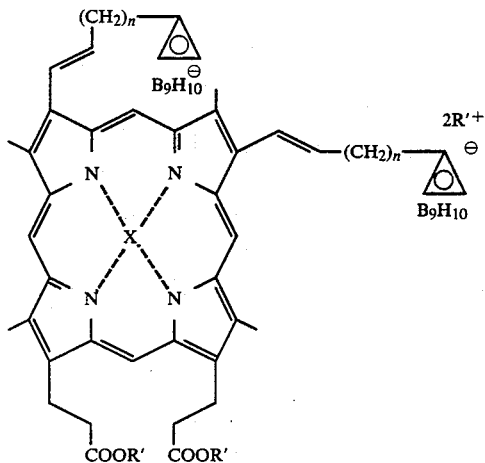

II wherein X is 2H or a bindable metal selected from the group consisting of zinc, iron, magnesium, manganese, cobalt, copper, germanium and gadolinium; R' is an alkali metal; and n is as defined above.

The compounds of formula II can be prepared following two distinct approaches. In the first approach, the diacid, that is the compound of formula I wherein R is hydrogen, is treated, in the presence of a suitable organic solvent, with methanol being preferred, with an alkali metal hydroxide, with potassium hydroxide being preferred. This approach yields the nido compound of formula II wherein X is 2H.

The bindable metal nido compound, that is the compound of formula II wherein X is, for example, zinc, is prepared by treating the carborated zinc dimethyl ester (not depicted in Reaction Scheme 1) of the formula

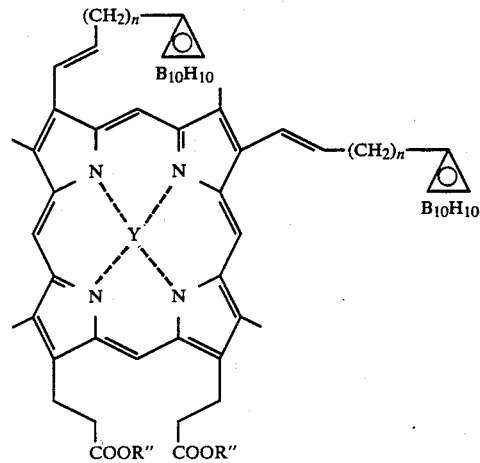

III wherein Y is a bindable metal selected from the group consisting of zinc, iron, magnesium, manganese, copper, cobalt, germanium and gadolinium; R" is lower alkyl containing 1 to 6 carbon atoms; and n is as defined above,
with an alkali metal hydroxide, preferably potassium hydroxide, in a suitable organic solvent, preferably methanol.

Neutron capture therapy requires that the patient be injected with a compound that totally or at least partially accumulates in a tumor. The accumulating portion should include an element having an isotope, such as boron-10, that captures neutrons and emits alpha particles that destroy cells. For effective tumor destruction, the element should accumulate in the tumor so that the desired isotope is present in amounts of at least 10 ppm and preferably at least about 30 ppm. The isotope-containing compound should be generally nontoxic; however, recognizing the seriousness of the threat posed by malignant tumors, the use of mildly toxic chemicals may be tolerated. Furthermore, it is highly desirable that the compound accumulates preferentially in the tumor so that the tumor will be destroyed without excessive damage to normal tissues, such as blood capillaries.

The compounds of formula II are completely water soluble and upon injection there is a substantial uptake of the boron from these compounds in brain tumors. Thus these materials are preferred among the compounds of the present invention as the boronated drug in BNCT.

To accumulate the requisite amount of the boronated porphyrin compounds of the present invention in a tumor, generally a patient is injected with a dose of between about 2 grams and about 30 grams of the boronated porphyrin compound in a pharmaceutically acceptable medium between about 12 hours and about one month prior to subjecting the patient to the neutron beam.

Alternatively, multiple doses of the boronated porphyrin compounds of the present invention can be administered over a period of a few days prior to radiation treatment. The patient is positioned in front of the beam of neutrons so that the tumor is in the direct path of the beam. Typically, the patient's body is positioned between about 50 and 100 cm. from the beam port.

Thus, the present invention also comprises an improved method of treating a patient with a malignant tumor using BNCT which method comprises: administering to the patient a dose of a generally nontoxic compound including an element having an isotope that emits alpha particles when bombarded with neutrons, wherein the nontoxic compound is administered in a dosage sufficient to accumulate the isotope in the tumor in a concentration of at least 10 ppm; providing a source that emits neutrons having an energy distribution effective for neutron capture, through which a beam of neutrons is emitted; and positioning the patient so that said tumor is in the path of said beam for a time sufficient to effect substantial tumor tissue deterioration. The improvement of the present method comprises using as the generally nontoxic compound a dicarboranyl caged porphyrin of formulas I, II or III. The preferred di-carboranyl caged porphyrin is the water soluble bi-salt derivative, dipotassium 2,4-bis-[2-(1,2-dicarbaundecaborate(-1))ethenyl]deuteroporphyrin IX.

The invention will be more fully appreciated when considered in light of the following illustrative examples.

EXAMPLE 1

The preparation of the compounds of formula I is shown in Reaction Scheme 1. A preselected amount of naturally occurring metalloporphyrin hemin is placed in a reaction flask and contacted with resorcinol under reaction conditions to produce a de-vinylized metalloporphyrin hemin derivative. The de-vinylized hemin derivative is then treated with iron (II) sulfate, hydrogen chloride, and methanol under Grinstein reaction conditions to obtain a demetallized product which is deuteroporphyrin IX DME. The di-methyl ester porphyrin is treated with the metallic reagent zinc (II) acetate in methanol and methylene chloride at room temperature to produce a zinc porphyrin dimethyl ester in a 96% yield. The di-methyl ester metalloporphyrin is then contacted with mercury (II) acetate (3.9 molar equivalent) in dry tetrahydrofuran (THF) and dry methanol at 60° C. under $N_2$ for five hours. Aqueous sodium chloride is used to from the chloride salt. The product is extracted with methylene chloride (suspension) and washed with water, dried, and the solvent is removed to obtain a 3,8-mercuric chloride substituted di-methyl ester metalloporphyrin in quantitative yield.

An alkylation is then performed on the dimercuric metalloporphyrin. A lithium palladium chloride solution is generated with lithium chloride (1.8 molar equivalents), palladium chloride (2.6 molar equivalents) and dry acetonitrile at reflux for thirty minutes. The dimercuric metalloporphyrin in dry THF and dry dimethylsulfoxide (DMSO) is treated with the lithium palladium chloride ($LiPdCl_3$) solution under $N_2$ atmosphere at 50° C. Vinyl-o-carborane (30 to 50 molar equivalents) is then added to the palladium complex. After thirty minutes to one hour at 50° C., the reaction mixture is cooled. The solution is then filtered through Celite, diluted with methylene chloride, washed with water, dried, and stripped of solvent to obtain a di-carboranyl caged metalloporphyrin. The di-carboranyl caged metalloporphyrin is purified by flash chromatography (silica) and eluted with a 1:1 mixture of petroleum ether or hexane and methylene chloride to remove excess vinyl-o-carborane reagent. The purified metalloporphyrin is then treated with 1% methanol in methylene chloride. If formed, the mono-carboranyl caged metalloporphyrin can be removed with 2% methanol in methylene chloride. After recrystallization in methanol/methylene chloride, there is obtained the di-carboranyl caged metalloporphyrin of formula III wherein R" is methyl which gives the following proton NMR spectrum (in $CDCl_3$): 9.963 (s, 1H, meso); 9.913 (s, 1H, meso); 9.852 (s, 2H, meso); 8.451 (d, 2H, vinyl J=15.9 Hz); 8.867 (d, 1H, vinyl J=15.7 Hz); 6.852 (d, 1H, vinyl J=15.7 Hz); 4.308 (t, 4H, $CH_2CH_2CO_2H$); 4.786 (s, 2H, carborane CH); 3.6044, 3.587, 3.533 (s, 6H, methyl x3); 3.214 (t, 4H, $CH_2CO_2H$); 3.2-1.4 (br s, 20H, B - H).

The di-carboranyl caged metalloporphyrin is then treated with trifluoroacetic acid (TFA) under $N_2$ atmosphere to remove the zinc and obtain a di-carboranyl caged porphyrin product. The product is recrystallized in methanol/methylene chloride to obtain a red brick powder in 42% yield. There is obtained the di-carboranyl caged porphyrin of formula I wherein R is methyl which gives the following proton NMR spectrum (in $CDCl_3$): 10.077 (s, 2H, meso); 9.982 (s, 1H, meso); 9.944 (s, 1H, meso); 8.421 (d, 2H, vinyl, J=15.8 Hz); 6.924 (d, 2H, vinyl, J=15.9 Hz); 6.907 (d, 1H, vinyl, J=15.8 Hz); 4.395 (t, 4H, —$CH_2CH_2CO_2Me$); 4.113 (s, 2H, carborane CH); 3.656 (s, 9H, methyl); 3.624 (s, 6H, methyl); 3.617 (s, 3H, methyl); 3.276 (t, 4H, $CH_2CO_2Me$); 3.8-1.5 (br mult., 20 BH); −3.623 (s, 2H, NH).

Chemical analysis gives $C_{40}H_{58}N_4O_4B_{20}$ when the dicarboranyl caged porphyrin is analyzed by elemental analysis. An ultraviolet (UV)-visible spectrum (in methylene chloride) for the di-carboranyl caged porphyrin is:

416 (178,000), 511 (16,500), 546 (15,200), 580 (6,860), 634 (5,220).

The di-carboranyl caged porphyrin compound is then treated with 2N HCl and THF to hydrolize the methyl esters. The reaction yields the di-nidocarboranyl caged di-propionic acid porphyrin of formula I wherein R is hydrogen having the following proton NMR spectrum (in deuterated THF):

10.174 (s, 1H, meso); 10.118 (s, 1H, meso); 10.087 (s, 1H, meso); 10.035 (s, 1H, meso); 8.531 (d, 2H, vinyl J=15.8 Hz); 7.147 (d, 2H, vinyl J=15.8 Hz); 7.116 (d, 1H, vinyl J=15.7 Hz); 5.201 (s, 2H, carborane CH); 4.331 (q, 4H, $CH_2CH_2CO_2H$); 3.187 (s, H, methyl); 3.203 (q, 4H, $CH_2CO_2H$); −3.754 (s, 2H, NH).

EXAMPLE 2

To increase water solubility the di-carboranyl caged dipropionic acid porphyrin from Example 1 is treated with methanolic potassium hydroxide (KOH) at reflux for 3 hours to obtain an ionized di-nidocarboranyl caged di-propionic acid porphyrin. The ionized product is the compound of formula II wherein X is 2H and R' is K which contains two degraded nidocarboranyl cages, each cage having one less boron atom. Said product gives the following proton NMR (in deuterated methanol): 9.671 (s, 1H, meso); 9.585 (s, 1H, meso); 9.158 (s, 1H, meso); 8.934 (s, 1H, meso); 7.425 (d, 1H, vinyl J=16.0 Hz); 7.343 (d, 1H, vinyl J=15.9 Hz); 6.881 (d, 1H, vinyl J=16.1 Hz); 6.796 (d, 1H, vinyl J=16.0 Hz); 4.44-4.35 (m, 4H, $CH_2CH_2CO_2H$); 3.611, 3.584, 3,584, 3.542 (s, 3H, methyl x4); 2.169 (s, 2H, carborane CH); −2.078 (br s, 4H, NH and BH-1).

EXAMPLE 3

The dicarboranyl caged di-methyl ester metallo(zinc)porphyrin, the compound of formula III wherein R" is methyl, prepared in Example I above is treated directly with methanolic KOH to concomitantly degrade the cages and saponify the esters. The product from the reaction is the ionized di-nidocarboranyl caged di-propionic acid metalloporphyrin of formula II wherein X is Zn and R' is K. The ionized product gives the following proton NMR (in deuterated methanol): 10.043 (s, 2H, meso); 9.936 (s, 2H, meso); 7.758 (d, 1H, vinyl J=16.0 Hz); 7.733 (d, 1H, vinyl J=15.9 Hz); 6.879 (d, 1H, vinyl J=15.8 Hz); 6.845 (d, 1H, vinyl J=16.0 Hz); 4.354 (t, 4H, $CH_2CH_2CO_2H$); 3.251 (t, 4H, $CH_2CH_2H$); −2.40 (br s, 2H, BH—).

EXAMPLE 4

The porphyrins of the present invention were tested for biodistribution and tumor uptake. BALB/c mice carrying transplanted Harding-Passey melanomas subcutaneously on the thigh or abdomen were given six intraperitoneal 0.5 mL injections over two days. The injection solutions contained 1 mg of compound/mL which is a total dose of 3 mg/mouse (approx. 150 $\mu g$ porphyrin/g body weight or 32.2 $\mu g$ B/g body weight).

The compounds of formula II were completely water soluble and were allowed a 2 day clearance period post injection. The boron content was assayed by prompt gamma analysis using the gamma ray from the $^{10}B(n,\alpha)^7Li$ reaction. Counts from the 478 MeV prompt-$\tau$-ray are detected and analyzed using a narrow collimated thermal neutron beam from the Medical Research Reactor at Brookhaven National Laboratory. In this method the mice are dissected and whole organs or tissue samples (0.20–1.0 g) are measured for their boron content.

Table 1 shows that there is substantial uptake of boron into the tumor while Table 1 shows retention of boron in the tumor with clearance from the blood over time. Table 1 provides data for both the free base (compound of formula II wherein X is 2H) as well as the zinc chelate (compound of formula II wherein X is Zn), while Table 2 provides data for the free base. The tumor to blood ratio is higher for the free base and is approximately 1:1 at 2 days post-injection but increases to approx. 5:1 after 4 days clearance. The long retention of porphyrins in tumor tissue can be exploited by waiting at least 4 days after it has cleared out of the blood before irradiation.

From both the free base and the zinc chelate there is only a small amount of boron in the normal brain, indicating that this compound does not cross the blood-brain barrier.

As will be evident to those skilled in the art, various modifications on this invention can be made or followed, in light of the foregoing disclosure and illustrative examples, tables and discussion, without departing from the spirit and scope of the disclosure or from the scope of the invention as set forth in the following claims.

TABLE 1[a]

| UPTAKE OF THE FREE BASE AND THE ZINC CHELATE (2 DAY CLEARANCE) IN μgB/g TISSUE | | |
|---|---|---|
| TISSUE | FREE BASE | ZN CHELATE |
| Tumor | 18.7 ± 3.4 | 15.7 ± 2.4 |
| Liver | 38.0 ± 11.9 | 48.4 ± 13.4 |
| Blood | 15.3 ± 1.5 | 20.0 ± 1.3 |
| Brain[b] | 2.0 | 0 |
| Muscle | 3.9 | 8.7 |
| Lung[b] | 20.8 | 14.0 |
| Kidney[b] | 16.8 | 32.5 |
| Spleen[b] | 8.5 | 12.3 |

[a]Mice received 6 I.P. injections of 3 mg of the free base or of the zinc chelate in 3 ml water, pH 7
[b]Mice tissues were pooled on-1 used for standard durations

TABLE 2

| UPTAKE OF THE FREE BASE IN MOUSE TISSUES (≧2 MICE/POINT, 32 μg B/g DOSE) IN μg/g | | | |
|---|---|---|---|
| TISSUE | 2 DAY | 4 DAY | 6 DAY |
| Tumor | 18.7 ± 3.4 | 13.6 ± 2.0 | 17.0 ± 6.0 |
| Liver | 38.0 ± 11.9 | 37.8 ± 5.9 | 35.2 ± 1.8 |
| Blood | 15.3 ± 1.5 | 2.5 ± 1.8 | 4.5 ± 1.2 |
| Brain | 2.0 | .21 | .78 |
| Muscle | 3.9 | 6.4 | 10.2 |
| Lung | 20.8 | 14.6 | 12.4 |
| Kidney | 16.8 | 12.8 | 10.4 |
| Spleen | 8.5 | 13.4 | 11 |

We claim:

1. A compound of the formula

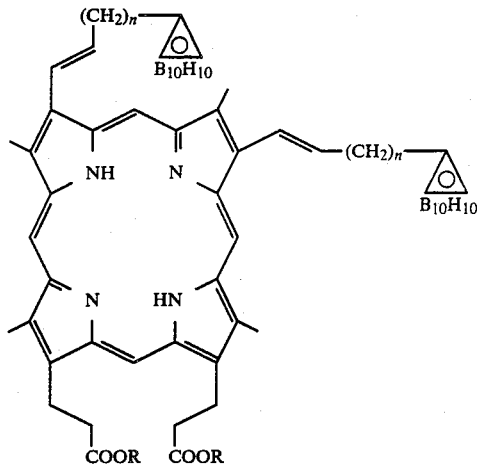

wherein R is hydrogen or lower alkyl having 1 to 6 carbon atoms and n is 0 to 10.

2. 3,8-(1,1¹(2,2¹-bis-(1,2-dicarbadodecaboranyl)-ethenyl) 13,17-dipropionic acid-2,7,12,18-tetramethylporphyrin dimethyl ester.

3. 3,8-(1,1¹(2,2¹-bis-(1,2-dicarbadodecaboranyl)-ethenyl) 13,17-dipropionic acid-2,7,12,18-tetramethylporphyrin.

4. A compound of the formula

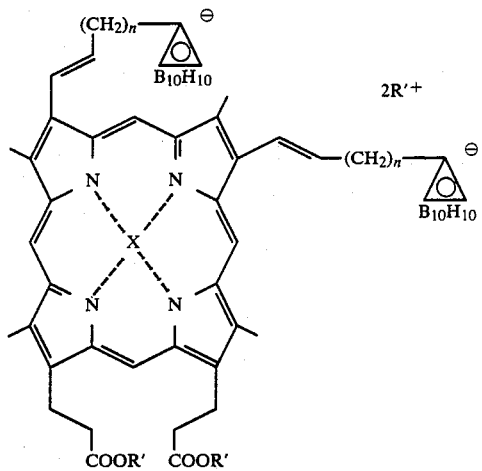

wherein X is 2H or a bindable metal selected from the group consisting of zinc, iron, magnesium, manganese, copper, cobalt, germanium and gadolinium; R' is an alkali metal; and n is 0 to 10.

5. Dipotassium 3,8-(1,1¹(2,2¹-bis-(7,8-dicarbaundecaborate)-1))ethenyl)-13,17-dipropionic acid-2,7,12,18-tetramethyl porphyrin.

6. A compound of the formula

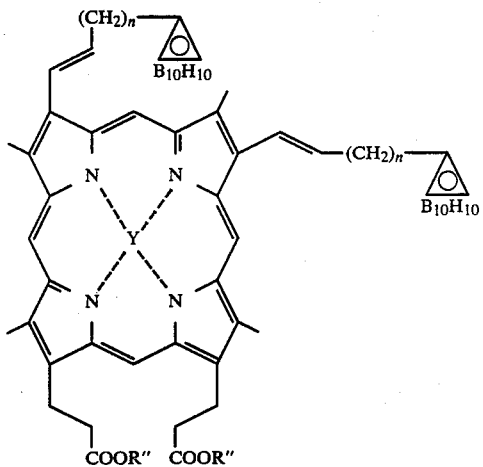

wherein Y is a bindable metal selected from the group consisting of zinc, iron, magnesium, manganese, copper, cobalt, germanium and gadolinium; R" is a lower alkyl group containing 1 to 6 carbon atoms; and n is 0 to 10.

7. The compound of claim 6 wherein Y is zinc, R" is methyl and n is 0.

8. A method of treating malignant brain tumors using Boron Neutron Capture Therapy wherein the boron drug employed is 3,8-(1,1$^1$(2,2$^1$-bis-(1,2-dicarbadodecaboranyl)ethenyl) 13,17-dipropionic acid-2,7,12,18-tetramethylporphyrin.

9. A method of treating malignant brain tumors using Boron Neutron Capture Therapy wherein the boron drug employed is dipotassium 3,8-(1,1$^1$(2,2$^1$-bis-(7,8-dicarbaundecaborate-(-1))ethenyl)-13,17-dipropionic acid-2,7,12,18-tetramethyl porphyrin.

10. In a method of treating a patient with a malignant tumor which comprises administering to the patient a dose of a generally nontoxic compound which contains an element having an isotope that emits alpha particles when bombarded with neutrons, said compound being administered in a dosage sufficient to accumulate said isotope in the tumor in a concentration of at least 10 ppm; providing a source that emits neutrons having an energy distribution effective for neutron capture, said source having a port through which a beam of neutrons is emitted; and positioning the patient so that said tumor is in the path of said beam for a time sufficient to effect substantial tumor tissue deterioration; the improvement comprising using as the generally nontoxic compound a 3,8-(1,1'(2,2'-bis-(7,8-dicarbaundecaborate(-1)alkenyl) porphyrin derivative.

11. A process according to claim 10 wherein the dicarboranyl caged porphyrin comprises dipotassium 3,8-(1,1$^1$-(2,2$^1$-bis-(7,8-dicarbaundecaborate(-1)ethenyl)-13,17-diproprionic acid-2,7,12,18-tetramethylporphyrin.

12. A process according to claim 10 wherein the dicarboranyl caged porphyrin comprises 3,8-(1,1$^1$(2,2$^1$-bis-(7,8-dicarbaundecaborate(-1))ethenyl)-13,17-dipropionic acid -2,7,12,18-tetramethylporphyrin.

* * * * *